United States Patent
Boehm et al.

[11] Patent Number: 5,998,654
[45] Date of Patent: Dec. 7, 1999

[54] RETINOIC ACID RECEPTOR ANTAGONIST COMPOUNDS AND METHODS

[75] Inventors: Marcus F. Boehm; Lin Zhang, both of San Diego, Calif.

[73] Assignee: Ligand Pharmaceuticals Incorporated, San Diego, Calif.

[21] Appl. No.: 08/901,014

[22] Filed: Jul. 25, 1997

[51] Int. Cl.$^6$ .......................... C07C 229/00; A01N 37/10
[52] U.S. Cl. ............................ 560/45; 560/104; 562/433; 562/451; 564/163; 564/167; 514/532; 514/568; 514/617; 514/619
[58] Field of Search ............................ 560/104, 45, 433, 560/451; 564/163, 162; 514/532, 568, 617, 619

[56] References Cited

U.S. PATENT DOCUMENTS

| | | |
|---|---|---|
| 5,466,861 | 11/1995 | Dawson . |
| 5,514,821 | 5/1996 | Bennani . |
| 5,552,271 | 9/1996 | Pfahl . |
| 5,668,175 | 9/1997 | Evans . |
| 5,705,167 | 1/1998 | Bernardon .............................. 560/104 |
| 5,712,093 | 1/1998 | Pfahl et al. . |
| 5,721,103 | 2/1998 | Boehm . |
| 5,780,676 | 7/1998 | Boehm . |

FOREIGN PATENT DOCUMENTS

| | | |
|---|---|---|
| 9311755 | 6/1993 | WIPO . |
| 9632935 | 10/1996 | WIPO . |
| 9712853 | 4/1997 | WIPO . |

*Primary Examiner*—Paul J. Killos
*Attorney, Agent, or Firm*—James Scott Elmer

[57] ABSTRACT

Trienoic compounds having activity as antagonists for retinoic acid receptors are provided. Also provided are pharmaceutical compositions incorporating such compounds and methods for their therapeutic use.

29 Claims, No Drawings

RETINOIC ACID RECEPTOR ANTAGONIST COMPOUNDS AND METHODS

FIELD OF THE INVENTION

The present invention relates to compounds having activity as antagonists of retinoic acid receptors, and to methods for the therapeutic use of such compounds.

BACKGROUND OF THE INVENTION

The vitamin A metabolite, retinoic acid, has long been recognized to induce a broad spectrum of biological effects. In addition, a variety of structural analogues of retinoic acid have been synthesized that also have been found to be bioactive. Some, such as Retin-A® and Accutane®, have found utility as therapeutic agents for the treatment of various pathological conditions. In addition, synthetic retinoids have been found to mimic many of the pharmacological actions of retinoic acid.

Medical professionals have become very interested in the therapeutic applications of retinoids. Among their uses approved by the FDA is the treatment of severe forms of acne and psoriasis. A large body of evidence also exists that these compounds can be used to arrest and, to an extent, reverse the effects of skin damage arising from prolonged exposure to the sun. Other evidence exists that these compounds may be useful in the treatment and prevention of a variety of cancerous and pre-cancerous conditions, such as melanoma, cervical cancer, some forms of leukemia, oral leukoplakia and basal and squamous cell carcinomas. Retinoids have also shown an ability to be efficacious in treating and preventing diseases of the eye, cardiovascular system, immune system, skin, respiratory and digestive tracts, and as agents to facilitate wound healing and modulate programmed cell death (apoptosis).

Major insight into the molecular mechanism of retinoic acid signal transduction was gained in 1988, when a member of the steroid/thyroid hormone intracellular receptor superfamily was shown to transduce a retinoic acid signal. Evans, *Science*, 240:889–95 (1988); Giguere et al., *Nature*, 330:624–29 (1987); Petkovich et al., *Nature*, 330: 444–50 (1987). It is now known that retinoids regulate the activity of two distinct intracellular receptor subfamilies; the Retinoic Acid Receptors (RARs) and the Retinoid X Receptors (RXRs), including their isoforms, RARα, β, γ and RXRα, β,γ. In this regard, an endogenous low-molecular-weight ligand which modulates the transcriptional activity of the RARs is all-trans-retinoic acid (ATRA), while an endogenous ligand for the RXRs is 9-cis retinoic acid (9-cis). Heyman et al., *Cell*, 68:397–406 (1992) and Levin et al. *Nature*, 355:359–61 (1992).

Although both the RARs and RXRs respond to ATRA in vivo, due to the in vivo conversion of some of the ATRA to 9-cis, the receptors differ in several important aspects. First, the RARs and RXRs are significantly divergent in primary structure (e.g., the ligand binding domains of RARα and RXRα have only 27% amino acid identity). These structural differences are reflected in the different relative degrees of responsiveness of RARs and RXRs to various vitamin A metabolites and synthetic retinoids. In addition, distinctly different patterns of tissue distribution are seen for RARs and RXRs. For example, in contrast to the RARs, which are not expressed at high levels in the visceral tissues, RXRα mRNA has been shown to be most abundant in the liver, kidney, lung, muscle and intestine. Finally, the RARs and RXRs have different target gene specificity. For example, response elements have recently been identified in the cellular retinal binding protein type II (CRBPII) and Apolipoprotein AI genes which confer responsiveness to RXR, but not RAR. Furthermore, RAR has also been recently shown to repress RXR-mediated activation through the CRBPII RXR response element (Manglesdorf et al., *Cell*, 66:555–61 (1991)). These data indicate that two retinoic acid responsive pathways are not simply redundant, but instead manifest a complex interplay.

In view of the related, but clearly distinct, nature of these receptors, retinoids which are more selective for the RAR subfamily than the RXR subfamily provide the capacity for independent control of the physiologic processes mediated by the RARs versus RXRs. While offering the distinct therapeutic advantages noted above, RAR agonists also manifest an array of undesired side effects, depending upon the therapeutic dose level employed, including, but not limited to, headache, teratogenesis, mucocutaneous toxicity, musculoskeletal toxicity, dyslipidemias, skin irritation and hepatotoxicity, as well as the relatively rare, but serious, medical condition, hypervitaminosis A syndrome, which typically results from excessive intake of vitamin supplements. These side effects and conditions place limits on the application of RAR agonists in the treatment of various disease states.

Structurally distinct RAR antagonists have been previously described. See, e.g., PCT Application WO 94/14777; Yoshimura et al., 38 *J. Med. Chem.*, 3163 (1995); Kaneko et al., 1 *Med. Chem. Res.*, 220 (1991); Apfel et al., 89 *Proc. Natl. Acad. Sci.*, 7129; Eckhardt et al., 70 *Toxicology Letters*, 299 (1994); Keidel et al., 14 *Molecular and Cellular Biology*, 287 (1994); and Eyrolles et al., 37 *J. Med. Chem.*, 1508 (1994). In addition, various polyene compounds have been disclosed to be useful in the treatment of inflammatory conditions, psoriasis, allergic reactions, and for use in sunscreens in cosmetic preparations. See eg., U.S. Pat. Nos. 4,534,979 and 5,320,833. Trienediolates of hexadienoic acids have also proved useful in the synthesis of retinoic and nor-retinoic acids. See M. J. Aurell, et al., 49 *Tetrahedron*, 6089 (1993). Further, trienoic retinoids have been shown to display both RAR and RXR agonist activity. See, PCT Patent Application WO 96/20913, published Jul. 11, 1996. However, no retinoid antagonist activity has been ascribed to these trienoic compounds.

SUMMARY OF THE INVENTION

The present invention provides trienoic compounds that have selective activity as antagonists of the Retinoic Acid Receptors (RARs). The present invention also provides labeled RAR antagonist compounds, pharmaceutical compositions incorporating these trienoic RAR antagonist compounds and methods for the therapeutic use of such compounds and pharmaceutical compositions.

These and various other advantages and features of novelty which characterize the invention are pointed out with particularity in the claims annexed hereto and forming a part hereof. However, for a better understanding of the invention, its advantages, and objects obtained by its use, reference should be had to the accompanying descriptive matter, in which there is illustrated and described preferred embodiments of the invention.

DEFINITIONS

In accordance with the present invention and as used herein, the following terms are defined with the following meanings, unless explicitly stated otherwise.

The term alkyl refers to straight-chain, branched-chain or cyclic structures that are optionally saturated or unsaturated (thereby resulting in alkenyl and alkynyl structures), as well as combinations thereof.

The term aryl refers to an optionally substituted six-membered aromatic ring.

The term heteroaryl refers to an optionally substituted five-membered or six-membered heterocyclic ring containing one or two heteroatoms selected from the group consisting of oxygen, nitrogen and sulfur, and more preferably one heteroatom selected from the group consisting of oxygen, nitrogen and sulfur. It will also be understood that the terms 'aryl' and 'heteroaryl' also encompass bi- and tri-aryls, bi- and tri-heteroaryls and any combination of up to three rings including at least one aryl fused to at least one heteroaryl, e.g., biphenyl, naphtyl, anthracenyl, furyl, pyrralyl, pyrralidinyl, thienyl, pyridyl, piperidyl, indolyl and quinolyl.

The terms RAR agonist compound(s) or RAR retinoid agonists refers to compounds that bind and/or activate one or more retinoid acid receptors (RARs), thereby affecting the transcriptional activity of a target gene to which the activated receptor and compound complex binds.

The terms RAR antagonist compound(s) refers to compounds that inhibit the activation of one or more Retinoic Acid Receptors in the presence of a known RAR agonist, thereby affecting the transcriptional activity of a target gene that would be up regulated but for the inhibitory activity of the RAR antagonist compound.

As used herein, isotopic labels or radiolabels refer to substituents labeled with deuterium, tritium, carbon 13 and/or carbon 14, including, but not limited to $^{14}CH_3$, $^{13}CH_3$, $CD_3$, $C^3H_3$, and $^{13}CD_3$.

DETAILED DESCRIPTION OF EMBODIMENTS OF THE INVENTION

In accordance with a first aspect of the present invention, we have developed RAR antagonist compounds having the formula:

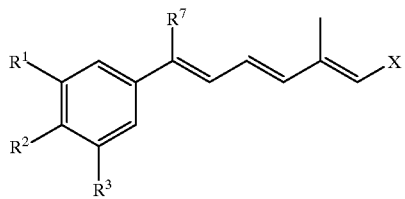

wherein:

$R^1$ and $R^3$ each independently are a $C_3$–$C_{10}$ alkyl, fluoroalkyl or perfluoroalkyl, an optionally substituted aryl, heteroaryl or arylalkyl, $NR^4$ or $NR^4R^5$, where $R^4$ and $R^5$ each independently are a $C_1$–$C_6$ alkyl, fluoroalkyl or perfluoroalkyl, or when $R^1$ is any of the above, then $R^3$ can be $OR^6$, where $R^6$ is a $C_3$–$C_{12}$ alkyl, fluoroalkyl or perfluoroalkyl;

$R^2$ is an optionally substituted aryl, heteroaryl, a $C_4$–$C_{12}$ alkyl, fluoroalkyl or perfluoroalkyl optionally substituted with $^{14}CH_3$, $^{13}CH_3$, $CD_3$, $C^3H_3$, and/or $^{13}CD_3$, $OR^6$, where $R^6$ has the definition given above, or $R^2$ can be hydrogen, $OCH_3$ or $OCH_2CH_3$ if $R^1$ and/or $R^3$ are an aryl or heteroaryl linked by a $C_1$–$C_{12}$ alkyl, fluoroalkyl or perfluoroalkyl;

$R^7$ is hydrogen, F, Cl, Br, I, CF3 or a $C_1$–$C_2$ alkyl optionally substituted with $^{14}CH_3$, $^{13}CH_3$, $CD_3$, $C^3H_3$, and/or $^{13}CD_3$;

X is $COOR^8$, $CONR^9$, or $CONHR^9R^{10}$ where $R^8$ represents hydrogen or a $C_1$–$C_6$ alkyl, and where $R^9$ and $R^{10}$ each independently represent a $C_1$–$C_6$ alkyl, or an aryl or heteroaryl optionally substituted with OH, F, Br, Cl or I, provided, however, that $R^9$ and $R^{10}$ both cannot be an aryl or heteroaryl.

Preferably, $R^1$ and $R^3$ independently represent a $C_3$–$C_{10}$ alkyl and $R^2$ represents a $C_4$–$C_8$ alkyl, more preferably $R^1$ and $R^3$ independently represent a $C_3$–$C_4$ alkyl and $R^2$ represents a $C_4$–$C_6$ alkyl.

The compounds of the present invention also include all pharmaceutically acceptable salts, as well as esters, amides and prodrugs. Preferably, such salts, esters and amides, will be formed at the $R^8$, $R^9$ and/or $R^{10}$ positions. As used in this disclosure, pharmaceutically acceptable salts include, but are not limited to: pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydoxymethyl) aminomethane. Additional pharmaceutically acceptable salts are known to those skilled in the art.

The compounds of the present invention exhibit RAR antagonist activity and are particularly useful in the treatment of the chronic and/or acute toxicity and side effects due to RAR agonist (retinoid) therapy. Thus, the compounds of the present invention can be individually administered in response to a particular condition, e.g., hypervitaminosis A syndrome, or can be co-administered as an adjunct to RAR agonist therapy, to prevent the occurrence of one or more of the associated side effects, e.g., as a topical cream to relieve the mucocutaneous toxicology side effects to RAR agonist therapy. In this regard, an example of a particularly severe toxicity is hypervitaminosis A syndrome, which is manifested by RAR agonists, including naturally occurring Vitamin A and its precursors. The symptoms associated with hypervitaminosis A syndrome, as well as general side effects from RAR agonist therapy, include, but are not limited to, headache, skin irritation, skin peeling, bone toxicities, dislipidemias (e.g., hypertriglyceridemia), teratogenesis, mucocutaneous toxicity, musculoskeletal toxicity, and hepatotoxicity.

Disease states where RAR agonists are therapeutically employed, and therefore, where the side effects can be countered by the compounds of the present invention, include, but are not limited to, skin-related diseases (e.g., actinic and arsenic keratoses, inflammatory and non-inflammatory acne, psoriasis, ichthyoses, eczema, atopic dermatitis), in the prevention and treatment of cancerous and pre-cancerous conditions (e.g., cancers and pre-cancers of the breast, skin, prostate, cervix, uterus, colon, bladder, esophagus, stomach, lung, larynx, oral cavity, blood and lymphatic system and in the treatment of Kaposis sarcoma), diseases of the eye (e.g., proliferative vitreoretinopathy, retinal detachment and dry eye), in the treatment and prevention of various cardiovascular diseases (e.g., dyslipidemias, prevention of restenosis and as an agent to increase the level of circulating tissue plasminogen activator), in the prevention and treatment of conditions and diseases associated with human papilloma virus (HPV), inflammatory diseases (e.g., pulmonary fibrosis, ileitis, colitis and Krohn's disease), neurodegenerative diseases (e.g., Alzheimer's disease, Parkinson's disease and Amyotrophic Lateral Sclerosis), and in the modulation of apoptosis (e.g., induction of apoptosis and inhibition of T-Cell activated apoptosis). In addition, it will be understood by those skilled in the art that the RAR antagonist compounds of the present invention may also find application to potentiate certain of the RAR agonist therapeutic effects, e.g., in psoriasis.

Furthermore, it will be understood by those skilled in the art that the compounds of the present invention, including pharmaceutical compositions and formulations containing these compounds, can be used in a wide variety of combination therapies to treat the conditions and side effects described above. Thus, the compounds of the present invention can be used in combination with retinoid agonists, including where such retinoid agonists are used alone or in combination therapies, e.g., as chemotherapeutic agents such as cytostatic and cytotoxic agents, immunological modifiers such as interferons, interleukins, growth hormones and other cytokines, hormone therapies, surgery and radiation therapy.

Representative compounds of the present invention include, without limitation, 2E, 4E, 6E-[7-(3,5-Di-t-butyl-4-n-butoxyphenyl)-3-methyl]-octa-2,4,6-trienoic acid (Compound 7); 2E, 4E, 6E-[7-(3,5-Di-t-butyl-4-n-propoxyphenyl)-3-methyl]-octa-2,4,6-trienoic acid (Compound 8); 2E, 4E, 6E-[7-(3,5-Di-t-butyl-4-n-pentoxyphenyl)-3-methyl]-octa-2,4,6-trienoic acid (Compound 9); 2E, 4E, 6E-[7-(3,5-Di-t-butyl-4-n-hexoxyphenyl)-3-methyl]-octa-2,4,6-trienoic acid (Compound 10); 2E, 4E, 6E-[7-(3,5-Di-t-butyl-4-n-heptoxyphenyl)-3-methyl]-octa-2,4,6-trienoic acid (Compound 11); 2E, 4E, 6E-[7-(3,5-Di-t-butyl-4-n-octoxyphenyl)-3-methyl]-octa-2,4,6-trienoic acid (Compound 12); (2E,4E,6E)-7-[3-t-butyl-5-(1-phenyl-vinyl)-phenyl]-3-methyl-octa-2,4,6-trienoic acid (Compound 17); and 2E, 4E, 6E-[7-(3,5-Di-t-butyl-4-{[4,5-$^3H_2$]-n-pentoxy}phenyl)-3-methyl]-octa-2,4,6trienoic acid (Compound 20).

The compounds of the present invention can be obtained by routine chemical synthesis by those skilled in the art, e.g., by modification of the compounds disclosed or by a total synthesis approach. In this regard, the synthesis of the compounds of the present invention follows well established retinoid synthesis schemes and techniques as described in M. I. Dawson and W. H. Okamura, "Chemistry and Biology of Synthetic Retinoids", Chapters 3, 8, 14 and 16, CRC Press, Inc., Florida (1990); M. I. Dawson and P. D. Hobbs, *The Synthetic Chemistry of Retinoids*, In Chapter 2: "The Retinoids, Biology, Chemistry and Medicine", M. B. Sporn et al., Eds. (2nd ed.), Raven Press, New York, N.Y., pp. 5–178 (1994) and R. S. H. Liu and A. E. Asato, "Photochemistry and Synthesis of Stereoisomers of Vitamin A," 40 *Tetrahedron*, 1931 (1984), the disclosures of which are herein incorporated by reference. The sequence of steps of the general methods of synthesizing the compounds of the present invention are shown below. In addition, more detailed and illustrative synthetic schemes for specific compounds of the present invention will be found in the Examples included herein.

General Method

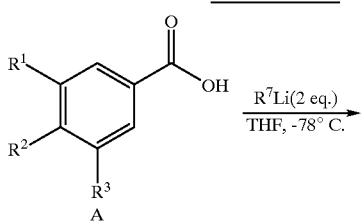

A

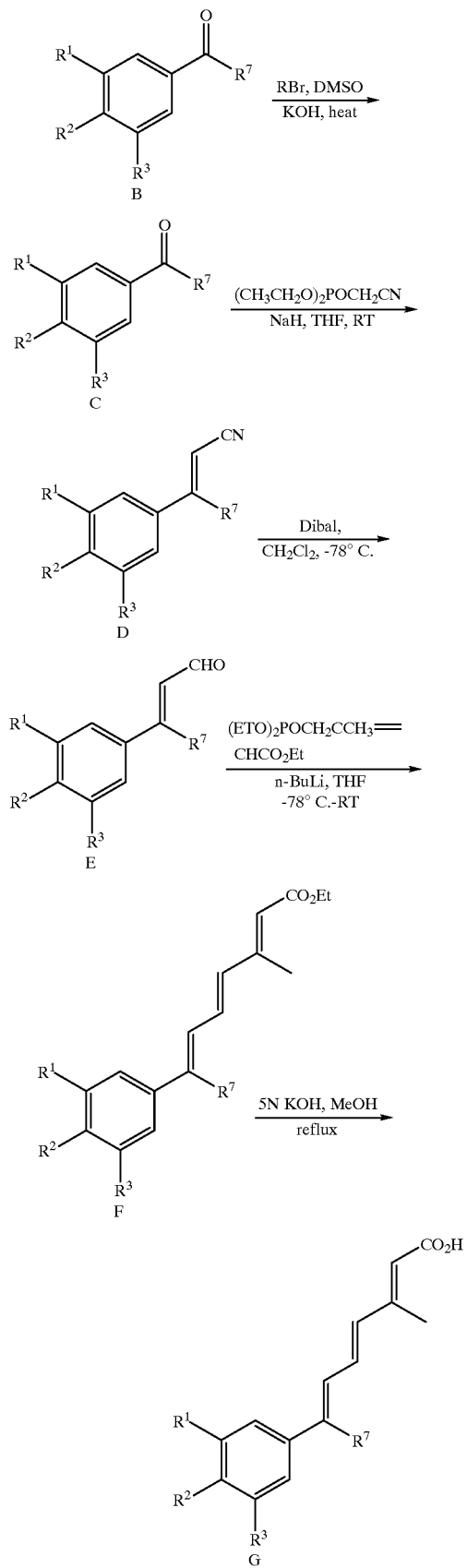

The compounds of the present invention may be prepared by treatment of aryl carboxylic acid A with an alkyl lithium reagent, such as methyl lithium, to give ketone B, which if $R^2$ is OH, may be alkylated with alkyl bromide to provide ketone C. Treatment of ketone C with a phosphonate, such as diethylcyanomethylphosphonate, to give nitrile D, followed by reduction of D in the presence of a reducing agent, such as diisobutyl aluminum hydride (Dibal), to provide aldehyde E. The cis and trans isomers of aldehyde E may be separated at this stage via thin-layer chromatography (TLC), or other recognized procedures known to those skilled in the art. The trans aldehyde of E is then treated with a phosphonate, such as triethyl-3-alkyl-4-phosphonocrotonate, to give the trienoate ester F, which in turn is saponified under basic conditions to give the carboxylic acid G.

It will be understood by those skilled in the art that certain modifications can be made to the above-described methods that remain within the scope of the present invention. For example, the compounds of the present invention may also be produced in the form of the corresponding amides or esters, and appropriate phosphoranes may be substituted for phosphonates. Furthermore, it will be understood that isotopic labels may be employed, including $^{13}CH_3$, $^{13}CD_3$, $^3H$, $^{14}C$ and the like. These labels may be introduced using the appropriate labeled reagents.

In another aspect, the RAR antagonist compounds, their pharmaceutically acceptable salts or hydrolyzable esters of the present invention are combined in a mixture with a pharmaceutically acceptable carrier to provide pharmaceutical compositions useful for treating the biological conditions or disorders noted herein in mammalian species, and more preferably, in human patients. The particular carrier employed in these pharmaceutical compositions may take a wide variety of forms depending upon the type of administration desired, e.g., intravenous, oral, topical, suppository or parenteral.

In preparing the compositions in oral liquid dosage forms (e.g., suspensions, elixirs and solutions), typical pharmaceutical media, such as water, glycols, oils, alcohols, flavoring agents, preservatives, coloring agents and the like can be employed. Similarly, when preparing oral solid dosage forms (e.g., powders, tablets and capsules), carriers such as starches, sugars, diluents, granulating agents, lubricants, binders, disintegrating agents and the like will be employed. Due to their ease of administration, tablets and capsules represent the most advantageous oral dosage form for the pharmaceutical compositions of the present invention.

For parenteral administration, the carrier will typically comprise sterile water, although other ingredients that aid in solubility or serve as preservatives, may also be included. Furthermore, injectable suspensions may also be prepared, in which case appropriate liquid carriers, suspending agents and the like will be employed.

For topical administration, the compounds of the present invention may be formulated using bland, moisturizing bases, such as ointments or creams. Examples of suitable ointment bases are petrolatum, petrolatum plus volatile silicones, lanolin, and water in oil emulsions such as Eucerin™ (Beiersdorf). Examples of suitable cream bases are Nivea™ Cream (Beiersdorf), cold cream (USP), Purpose Cream™ (Johnson & Johnson) hydrophilic ointment (USP), and Lubriderm™ (Warner-Lambert).

The pharmaceutical compositions and compounds of the present invention will generally be administered in the form of a dosage unit (e.g., tablet, capsule etc.) at from about 1 μg/kg of body weight to about 500 mg/kg of body weight, more preferably from about 10 μg/kg to about 250 mg/kg, and most preferably from about 20 μg/kg to about 100 mg/kg. As recognized by those skilled in the art, the particular quantity of pharmaceutical composition according to the present invention administered to a patient will depend upon a number of factors, including, without limitation, the biological activity desired, the condition of the patient, and tolerance for the drug.

The compounds of this invention also have utility when labeled and used in assays to determine the presence of RARs. They are particularly useful due to their ability to selectively bind to RAR members and can therefore be used to determine the presence of RAR isoforms in the presence of other retinoid receptors or related intracellular receptors.

Thus, the present invention also provides isotopically labeled and radiolabeled compounds, and methods for their synthesis, including deuterium, tritium, carbon 13 and carbon 14 labeled homologs. In a preferred aspect, the labeled compounds of the present invention display a specific activity of at least 15 Ci/mmol, and more preferably at least 25 Ci/mmol, and most preferably, at least 40 Ci/mmol. Such labeled compounds will also prove useful in the identification of compound metabolites in animal metabolism studies.

Due to the selective specificity of the compounds of this invention as antagonists of retinoid acid receptors, these compounds can also be used to purify samples of RARs in vitro. Such purification can be carried out by mixing samples containing retinoid acid receptors with one of more of the compounds of the present invention, so that the compound (ligand) binds to the receptor, and then separating out the bound ligand/receptor combination by separation techniques which are known to those of skill in the art. These techniques include column separation, filtration, centrifugation, tagging and physical separation, and antibody complexing, among others.

The antagonist compounds of the present invention also include racemate, individual stereoisomers and mixtures thereof. These isomers are then isolated by standard resolution techniques, including fractional crystallization and chiral column chromatography.

The antagonist compounds and pharmaceutical compositions of the present invention can advantageously be used in the treatment of the diseases and conditions described herein. In this regard, the antagonist compounds and pharmaceutical compositions of the present invention possess a number of advantages over previously identified retinoid antagonist compounds. For example, the compounds are extremely potent RAR antagonists as demonstrated in the co-transfection assay further described herein, preferably displaying 50% maximal inhibition (i.e., $IC_{50}$) of one or more of the retinoid acid receptors at a concentration of less than 100 nM, more preferably at a concentration of less than 50 nM, more preferably yet at a concentration of less than 20 nM, and most preferably at a concentration of less than 10 nM. Also, the RAR antagonist compounds of the present invention preferentially antagonize the activation of RARs at a potency level at least 2 times greater, preferably at least 5 times greater, more preferably at least 10 times greater, and most preferably at a potency level at least 100 times greater than the RXRs.

The invention will be further illustrated by reference to the following non-limiting Examples.

EXAMPLE 1

2E, 4E, 6E-[7-(3,5-Di-t-butyl-4-n-butoxyphenyl)-3-methyl]-octa-2,4,6-trienoic acid (Compound 7), prepared according to Scheme 1 illustrated below.

Scheme 1

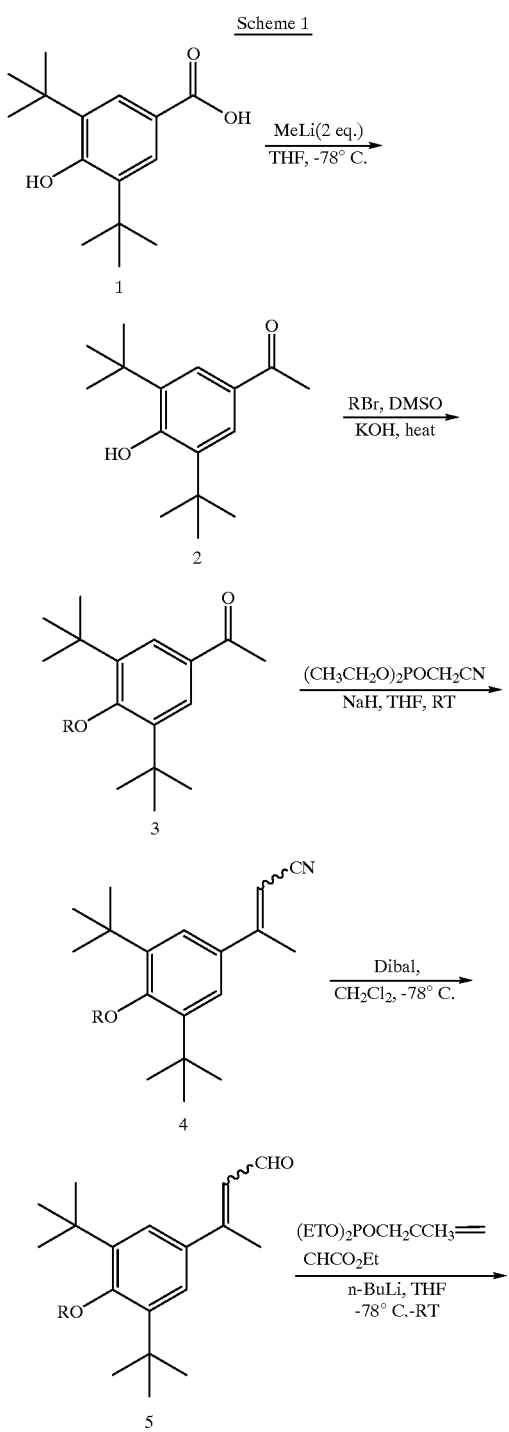

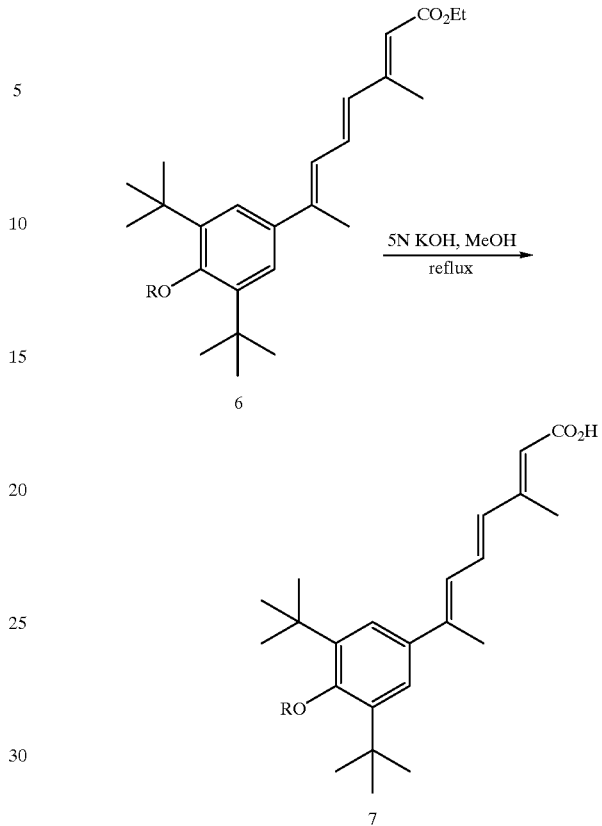

3,5-Di-t-butyl-4-hydroxyacetophenone 2. To 20.0 g (80.0 mmol) of 3,5-di-tertbutyl-4-hydroxybenzoic acid 1 in 100 mL of dry THF at −78° C. was added 183 mL (256 mmol) of a 1.4 N ether solution of MeLi. The reaction was slowly warmed to room temperature and stirred for an additional 30 m, then it was poured into saturated aqueous NH$_4$Cl (200 mL). The organic product was extracted with 1:1 EtOAc-hexanes (2×100 mL) dried (MgSO$_4$), filtered, concentrated and crystallized from ether-hexanes (2:5) to give 15.0 g (60.5 mmol) of ketone 2 (76% yield). TLC (5% EtOAc-95% hexanes) R$_f$ 0.4; $^1$H-NMR (CDCl$_3$) δ 1.47 (s, 18H, 6CH$_3$), 2.55 (s, 3H, CH$_3$), 5.73 (s, 1H, OH), 7.84 (s, 2H, Ar—CH).

3,5-Di-t-butyl-4-n-butoxyacetophenone 3. To 500 mg (2.02 mmol) of phenol 2 in 1 mL of dry DMSO was added 1 mL of n-propylbromide and 300 mg (5.35 mmol) of KOH. The mixture was stirred at 50° C. for 12 h followed by addition of H$_2$O (5 mL) and hexanes (10 mL). The hexane layer was separated and washed (2×5 mL of H$_2$O then 1×5 mL of brine), dried (MgSO$_4$) and concentrated to give 520 mg (1.79 mmol) of 3 which was used without further purification. TLC (5% EtOAc-95% hexanes) R$_f$ 0.5; $^1$H-NMR (CDCl$_3$) δ 1.01 (t, J=7.5 Hz, 3H, CH3), 1.43 (s, 18H, 6CH3), 1.42 (m, 2H, CH$_2$), 1.92 (m, 2H, CH2), 2.60 (s, 3H, CH3), 3.67 (t, J=7.5 Hz, 2H. CH2), 7.95 (s, 2H, Ar—CH).

3-(3,5-Di-t-butyl-4-n-butoxyphenyl)-but-2-enenitrile 4. To 1.00 g (5.59 mmol) of diethylcyanomethyl phosphonate in 5 mL of dry THF at −78° C. was added 2.2 mL (5.50 mmol) of 2.5 N nBuLi in hexanes. The reaction was warmed to RT and stirred for 30 min followed by addition of 500 mg (1.72 mmol) of ketone 3 in 5 mL of dry THF. After stirring for an additional 1 h, the reaction was quenched with saturated aqueous NH$_4$Cl (10 mL) and the products were extracted with hexane (2×10 mL). The hexane extracts were combined and washed (water then brine), dried (MgSO$_4$), filtered and concentrated to give 490 mg (1.49 mmol) of mainly the trans isomer of nitrile 4 which was used in the next step without further purification. TLC (5% EtOAc-95% hexanes) R$_f$ 0.6; $^1$H-NMR (CDCl$_3$) δ 1.00 (t, J=7.5 Hz, 3H, CH3), 1.47 (s, 18H, 6CH3), 1.45 (m, 2H, CH$_2$), 1.88 (m, 2H, CH2), 2.44 (s, 3H, CH3), 3.66 (t, J=7.5 Hz, 2H. CH2), 5.52 (s, 1H, CH═), 7.48 (s, 2H, Ar—CH).

3-(3,5-Di-t-butyl-4-n-butoxyphenyl)-but-2-enal 5. To 490 mg (1.49 mmol) of 4 in 5 mL of CH$_2$Cl$_2$ at −78° C. was added 2.31 mL (3.47 mmol) of a 1.5 M solution of DIBAL in toluene. After stirring for 15 m at −78° C., the reaction was quenched with 10 mL of a saturated aqueous solution of Rochelle salt. The product was extracted with ether (2×20 mL), washed (water then brine), dried (MgSO$_4$), filtered, concentrated and purified by chromatography (SiO$_2$, 3% EtOAc-hexanes) to give 460 mg (1.46 mmol) of 5 (98% yield). TLC (5% EtOAc-95% hexanes) R$_f$ 0.3; $^1$H-NMR (CDCl$_3$) δ 1.00 (t, J=7.5 Hz, 3H, CH$_3$), 1.40 (s, 18H, 6CH$_3$), 1.45 (m, 2H, CH$_2$), 1.89 (m, 2H, CH$_2$), 2.55 (s, 3H, CH$_3$), 3.68 (t, J=7.5 Hz, 2H, CH$_2$), 6.37 (d, J=8 Hz, 1H, CH═), 7.43 (s, 2H, Ar—CH).

2E, 4E, 6E-Ethyl-[7-(3,5-di-t-butyl-4-n-butoxyphenyl)-3-methyl]-octa-2,4,6-trienoate 6. To 1.0 g (3.79 mmol) of triethyl-3-methyl-4-phosphonocrotonate in 8 mL of dry 1:1 THF-DMPU at −78 ° C. was added 1.5 mL (3.75 mmol) of a 2.5 M nBuLi solution in hexanes and the reaction was warmed to RT. After stirring for 15 m, 490 mg (1.49 mmol) of the crude aldehyde 4 in 4 mL of dry 1:1 THF-DMPU was added. After stirring for 1 h at RT, the reaction was quenched with saturated aqueous NH$_4$Cl (20 mL) and the products were extracted with ether (2×20 mL). The combined ether extracts were washed (water then brine) dried (MgSO$_4$), filtered, concentrated and purified by column chromatography (SiO$_2$, 5% EtOAc-hexanes) to give 550 mg (1.29 mmol) of the crude ester 6 (87% yield). TLC (10% EtOAc-90% hexanes) R$_f$ 0.4; $^1$H-NMR (CDCl$_3$) δ 1.00 (t, J=7.5 Hz, 3H, CH$_3$), 1.28 (t, J=7.5 Hz, 3H, CH$_3$), 1.42 (s, 18H, 6CH$_3$), 1.45 (m, 2H, CH$_2$), 1.89 (m, 2H, CH$_2$), 2.24 (s, 3H, CH$_3$), 2.38 (s, 3H, CH$_3$), 3.68 (t, J=7.5 Hz, 2H. CH$_2$), 4.15 (m, 2H, CH$_2$), 5.80 (s, 1H, CH═), 6.32 (d, J=15 Hz, 1H, CH═), 6.50 (d, J=11 Hz, 1H, CH═), 7.02 (m, 1H, CH═), 7.34 (S, 2H, Ar—CH).

2E, 4E, 6E-[7-(3,5-Di-t-butyl-4-n-butoxyphenyl)-3-methyl]-octa-2,4,6-trienoic acid 7. To 500 mg (1.17 mmol) of ester 6 in 5 mL of MeOH was added 1 mL of 5N aqueous NaOH solution. The mixture was heated to reflux for 10 m, cooled to RT, acidified with 20% aqueous HCl solution and the organics extracted with ether (2×10 mL). The ether layer was washed (H$_2$O, brine), dried (MgSO$_4$), filtered and concentrated. Purification by preparative thin layer chromatography (SiO$_2$, 20% EtOAc-hexanes) followed by crystallization from ether-hexane (1:5) gave 320 mg (0.80 mmol) of the 2E,4E,6E-isomer 7 (69% yield). TLC (10% MeOH-90% CHCl$_3$) R$_f$ 0.6; mp 202–204° C. $^1$H-NMR (CDCl$_3$) δ 0.97 (t, J=7.4 Hz, 3H, CH$_3$), 1.43 (s, 18H, 6CH$_3$), 1.45 (m,2H,CH2), 1.85 (m, 2H, CH$_2$), 2.25 (s, 3H, CH$_3$), 2.39 (s, 3H, CH$_3$), 3.70 (t, J=7.4 Hz, 2H. CH$_2$), 5.84 (s, 1H, CH═), 6.40 (d, J=15 Hz, 1H, CH═), 6.51 (d, J=11 Hz, 1H, CH═), 7.06 (m, 1H, CH═), 7.35 (s, 2H, Ar—CH).

EXAMPLE 2

2E, 4E, 6E-[7-(3,5-Di-t-butyl-4-n-propoxyphenyl)-3-methyl]-octa-2,4,6-trienoic acid (Compound 8).

This compound was prepared in an analogous manner as 7, except that 3,5-di-t-butyl-4-n-propoxyacetophenone was used instead of 3,5-di-t-butyl-4-n-butoxyacetophenone: TLC (10% MeOH-90% CHCl$_3$) R$_f$ 0.6; mp 188–190° C.; $^1$H-NMR (CDCl$_3$) δ 0.98 (t, J=7.4 Hz, 3H, CH$_3$), 1.44 (s, 18H, 6CH$_3$), 1.88 (m, 2H, CH$_2$), 2.25 (s, 3H, CH$_3$), 2.39 (s, 3H, CH$_3$), 3.67 (t, J=7.4 Hz, 2H. CH$_2$), 5.84 (s, 1H, CH═), 6.40 (d, J=15 Hz, 1H, CH═), 6.52 (d, J=11 Hz, 1H, CH═), 7.06 (m, 1H, CH═), 7.35 (s, 2H, Ar—CH).

EXAMPLE 3

2E, 4E, 6E-[7-(3,5-Di-t-butyl-4-n-pentoxyphenyl)-3-methyl]-octa-2,4,6-trienoic acid (Compound 9).

This compound was prepared in an analogous manner as 7, except that 3,5-di-t-butyl-4-n-pentoxyacetophenone was used instead of 3,5-di-t-butyl-4-n-butoxyacetophenone: TLC (10% MeOH-90% CHCl$_3$) R$_f$ 0.6; mp 190–192° C.; $^1$H-NMR (CDCl$_3$) δ 0.93 (t, J=7.4 Hz, 3H, CH$_3$), 1.36 (m, 4H, 2CH$_2$), 1.43 (s, 18H, 6CH$_3$), 1.87 (m, 2H, CH$_2$), 2.25 (s, 3H, CH$_3$), 2.39 (s, 3H, CH$_3$), 3.70 (t, J=7.4 Hz, 2H. CH$_2$), 5.84 (s, 1H, CH═), 6.40 (d, J=15 Hz, 1H, CH═), 6.50 (d, J=11 Hz, 1H, CH═), 7.06 (m, 1H, CH═), 7.35 (s, 2H, Ar—CH).

EXAMPLE 4

2E, 4E, 6E-[7-(3,5-Di-t-butyl-4-n-hexoxyphenyl)-3-methyl]-octa-2,4,6-trienoic acid (Compound 10).

This compound was prepared in an analogous manner as 7, except that 3,5-di-t-butyl-4-n-hexoxyacetophenone was used instead of 3,5-di-t-butyl-4-n-butoxyacetophenone: TLC (10% MeOH-90% CHCl$_3$) R$_f$ 0.6; mp 154–156° C.; $^1$H-NMR (CDCl$_3$) δ 0.90 (t, J=7.4 Hz, 3H, CH$_3$), 1.34 (m, 6H, 3CH$_2$), 1.45 (s, 18H, 6CH$_3$), 1.85 (m, 2H, CH$_2$), 2.25 (s, 3H, CH$_3$), 2.40 (s, 3H, CH$_3$), 3.70 (t, J=7.4 Hz, 2H. CH$_2$), 5.84 (s, 1H, CH═), 6.40 (d, J=15 Hz, 1H, CH═), 6.51 (d, J=11 Hz, 1H, CH═), 7.06 (m, 1H, CH═), 7.35 (s, 2H, Ar—CH).

EXAMPLE 5

2E, 4E, 6E-[7-(3,5-Di-t-butyl-4-n-heptoxyphenyl)-3-methyl]-octa-2,4,6-trienoic acid (Compound 11).

This compound was prepared in an analogous manner as 7, except that 3,5-di-t-butyl-4-n-heptoxyacetophenone was used instead of 3,5-di-t-butyl-4-n-butoxyacetophenone: TLC (10% MeOH-90% CHCl$_3$) R$_f$ 0.6; mp 148–150° C.; $^1$H-NMR (CDCl$_3$) δ 0.89 (t, J=7.4 Hz, 3H, CH$_3$), 1.34 (m, 8H, 4CH$_2$), 1.44 (s, 18H, 6CH$_3$), 1.86 (m, 2H, CH$_2$), 2.25 (s, 3H, CH$_3$), 2.40 (s, 3H, CH$_3$), 3.70 (t, J=7.4 Hz, 2H. CH$_2$), 5.84 (s, 1H CH═), 6.40 (d, J=15 Hz, 1H, CH═), 6.51 (d, J=11 Hz, 1H, CH═), 7.06 (m, 1H, CH═), 7.35 (s, 2H, Ar—CH).

EXAMPLE 6

2E, 4E, 6E-[7-(3,5-Di-t-butyl-4-n-octoxyphenyl)-3-methyl]-octa-2,4,6-trienoic acid (Compound 12).

This compound was prepared in an analogous manner as 7, except that 3,5-di-t-butyl-4-n-octoxyacetophenone was used instead of 3,5-di-t-butyl-4-n-butoxyacetophenone: TLC (10% MeOH-90% CHCl$_3$) R$_f$ 0.6; mp 140–142° C.;

¹H-NMR (CDCl₃) δ 0.88 (t, J=7.4 Hz, 3H, CH₃), 1.31 (m, 10H, 5CH₂), 1.44 (s, 18H, 6CH₃), 1.86 (m, 2H, CH₂), 2.25 (s, 3H, CH₃), 2.40 (s, 3H, CH₃), 3.70 (t, J=7.4 Hz, 2H. CH₂), 5.84 (s, 1H, CH=), 6.40 (d, J=15 Hz, 1H, CH=), 6.51 (d, J=11 Hz, 1H, CH=), 7.06 (m, 1H, CH=), 7.35 (s, 2H, Ar—CH).

EXAMPLE 7

(2E,4E,6E)-7-[3-t-butyl-5-(1-phenyl-vinyl)-phenyl]-3-methyl-octa-2,4,6-trienoic acid (Compound 17), prepared according to Scheme 2 illustrated and described below.

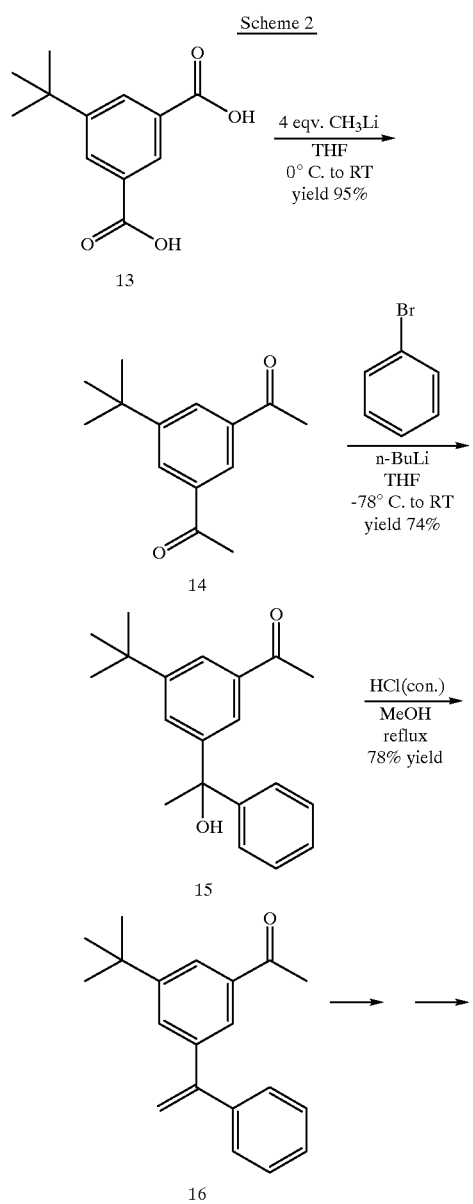

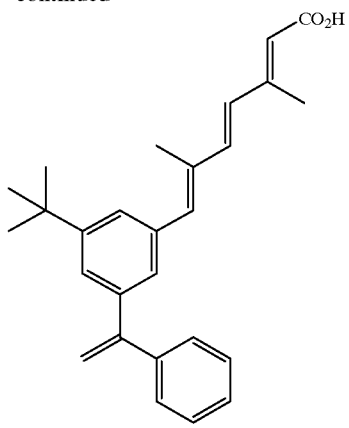

1-(3-Acetyl-5-t-butyl-phenyl)-ethanone 14. To 30.0 g (135.0 mmol) of 5-t butylisophthalic acid 13 in 350 ml of dry THF at −78° C. was added 405 ml (567 mmol) of MeLi (1.4 M in diethyl ether). The reaction mixture was slowly warmed to room temperature and stirred for an additional 30 min, then poured into saturated aqueous NH₄Cl (300ml). The product was extracted with hexanes (2×200 ml ), dried (MgSO₄), filtered, concentrated and purified by chromatography (SiO₂, 3% EtOAc-hexanes) to give 27.0 g of ketone 14 (94% yield): TLC (10% EtOAc-90% hexanes) R$_f$ 0.9; ¹H-NMR (CDCl₃) δ 1.39 (s, 9H, 3CH₃), 2.67 (s, 6H, 2COCH₃), 8.20 (d, J=1.5 Hz, 2H, Ar—H), 8.33 (t, J=1.5 Hz, 1H, Ar—H).

1-[3-t-butyl-5-(1-hydroxyl-1-phenyl-ethyl)-phenyl]-ethanone 15. To 288.0 mg (1.83 mmol) of bromobenzene in 8 ml of dry THF at −78° C. was added 734 ml (1.83 mmol) of n-BuLi (2.5 M in hexanes). The reaction was stirred for 10 min followed by addition of 400 mg (1.83 mmol) of diketone 14 in 2 ml of dry THF. After stirring for 30 min, the mixture was quenched with saturated aqueous NH₄Cl and the products were extracted with EtOAc. The EtOAc extracts were washed with water, brine, dried, filtered, and concentrated to give 420 mg of crude compound 15 which was used in the next step without further purification. TLC (20% EtOAC-80% hexanes) R$_f$ 0.7.

1-[3-t-butyl-5-(1-phenyl-vinyl)-phenyl]-ethanone 16. To 50.0 mg (0.17 mmol) of alcohol 15 in 4 ml of MeOH was added 2 drops of concentrated HCl. The mixture was heated at reflux for 5 min, cooled to RT, quenched with water, and the products extracted with ether. The ether layer was washed (water then brine), dried (MgSO₄), filtered and concentrated. Purification by preparative TLC (SiO₂, 5% EtOAc-95% hexanes) gave 33.0 mg (0.12 mmol) of 1-[3-t-butyl-5-(1-phenyl-vinyl)-phenyl]-ethanone 16 (71% yield). R$_f$ 0.8; ¹H-NMR (CDCl₃) δ 1.34 (s, 9H, 3CH₃), 2.58 (s, 3H, COCH3), 5.48 (s, 1H,CH=), 5.55 (s, 1H, CH=), 7.34 (m, 5H, Ar—H), 7.56 (t, J=3.7 Hz, 1H, Ar—H), 7.72 (t, J=3.7 Hz, 1H, Ar—H), 7.96 (t, J=3.7 Hz, 1H, Ar—H).

(2E,4E,6E)-7-[3-t-butyl-5-(1-phenyl-vinyl)-phenyl]-3-methyl-octa-2,4,6-trienoic acid 17. This compound was prepared in an analogous manner as 7, except that 1-[3-t-butyl-5-(1-phenyl-vinyl)-phenyl]-ethanone 16 was used instead of 3,5-di-t-butyl-4-n-butoxyacetophenone: TLC (10% MeOH-90% CHCl₃) R$_f$ 0.7; ¹H-NMR (CDCl₃) δ 1.33 (s, 9H, 3CH₃), 2.25 (s, 3H, CH3), 2.39 (s, 3H, CH3), 5.45 (s, 1H, CH=), 5.51 (s, 1H, CH=), 5.84 (s, 1H, CH=), 6.41 (d, J=15.1 Hz, 1H, CH=), 6.54 (d, J=11.2 Hz, 1H, CH=), 7.03 (m, 1H, CH=), 7.24 (t, J=3.7 Hz, 1H, Ar—H), 7.30 (t, J=3.7 Hz, 1H, Ar—H), 7.33 (m, 5H, Ar—H), 7.44 (t, J=3.7 Hz, 1H, Ar—H).

EXAMPLE 8

2E, 4E, 6E-[7-(3,5-Di-t-butyl-4-{[4,5-$^3$H$_2$]-n-pentoxy}phenyl)-3-methyl]-octa-2,4,6-trienoic acid (Compound 20), prepared according to Scheme 3 illustrated and described below.

Evaluation of Retinoid Receptor Subfamily Activity

Utilizing the "cis-trans" or "co-transfection" assay described by Evans et al., *Science*, 240:889–95 (May 13, 1988), the disclosure of which is herein incorporated by reference, the RAR antagonist compounds of the present

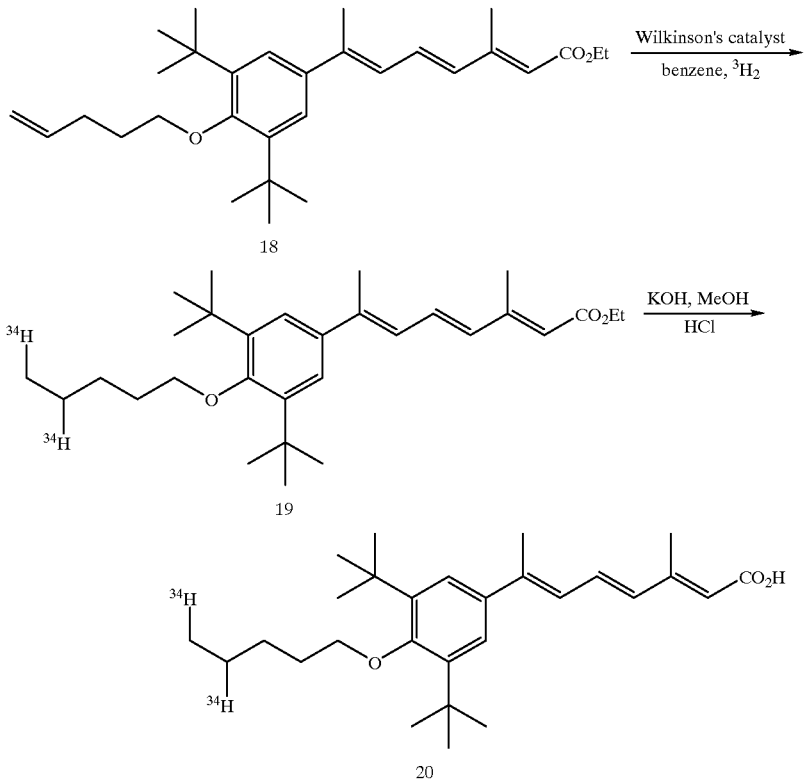

2E, 4E, 6E-[7-(3,5-Di-t-butyl-4-{[4,5-$^3$H$_2$]-n-pentoxy}phenyl)-3-methyl]-octa-2,4,6-trienoic acid 20. Wilkinson's catalyst (100 mg, 0.11 mmol) was suspended in 5 mL of benzene and the solution was degassed by freezing and degassing under vacuum, followed by addition of carrier-free $^3$H$_2$ gas. The catalyst was stirred under $^3$H$_2$ for 1 h followed by addition of 40 mg (0.09 mmol) of 18 in 1 mL of benzene. (Compound 18 was prepared in an analogous manner as 6, except that 3,5-di-t-butyl-4-n-pentenoxyacetophenone was used instead of 3,5-di-t-butyl-4-n-butoxyacetophenone). After stirring for 2 h under $^3$H$_2$ the reaction mixture was concentrated to dryness to remove all radioactive volatiles. The product was suspended in hexanes, chromatographed (SiO$_2$, 2% EtOAc-hexanes, pipette column) and concentrated to give 4.3 Ci of [$^3$H]-12 which was saponified with methanolic KOH at reflux. After hydrolysis of the ethyl ester was complete (by TLC), the reaction mixture was acidified and diluted with 5 mL of water. The organic product was extracted (EtOAc), washed (H$_2$O, brine), dried (MgSO$_4$), filtered, concentrated and crystallized from ether-hexanes to give 1.65 Ci of 99% pure material. The specific activity was 56 Ci/mmol.

$^1$H-NMR (CD$_3$OD) δ 0.88 (t, J=7.4 Hz, 3H, CH$_3$), 1.36 (m, 4H, 2CH$_2$), 1.43 (s, 18H, 6CH$_3$), 1.86 (m, 2H, CH$_2$), 2.23 (s, 3H, CH$_3$), 2.34 (s, 3H, CH$_3$), 3.70 (t, J=7.4 Hz, 2H. CH$_2$), 5.83 (s, 1H, CH=), 6.44 (d, J=15 Hz, 1H, CH=), 6.50 (d, J=11 Hz, 1H, CH=), 7.06 (m, 1H, CH=), 7.35 (s, 2H, Ar—CH). $^3$H-NMR-decoupled (CD$_3$OD) δ 0.93 (d, 1[$^3$H], J=7.7 Hz), 1.37 (d, 1[$^3$H], J=7.7 Hz).

invention were tested and found to have strong, specific activity as antagonists of RARs in the presence of RAR agonists. This assay is described in further detail in U.S. Pat. Nos. 4,981,784 and 5,071,773, the disclosures of which are incorporated herein by reference.

The co-transfection assay provides a method for identifying functional agonists which mimic, or antagonists which inhibit, the effect of native hormones or their mimics, and quantifying their activity for responsive IR proteins. In this regard, the co-transfection assay mimics an in vivo system in the laboratory. Importantly, activity in the co-transfection assay correlates very well with known in vivo activity, such that the co-transfection assay functions as a qualitative and quantitative predictor of a tested compounds in vivo pharmacology. See, eg., T. Berger et al. 41 *J. Steroid Biochem. Molec. Biol.* 773 (1992), the disclosure of which is herein incorporated by reference.

In the co-transfection assay, a cloned cDNA for an IR (e.g., human RARα:, RARβ, RXRγ) under the control of a constitutive promoter (e.g., the SV 40 promoter) is introduced by transfection (a procedure to induce cells to take up foreign genes) into a background cell substantially devoid of endogenous IRs. This introduced gene directs the recipient cells to make the IR protein of interest. A second gene is also introduced (co-transfected) into the same cells in conjunction with the IR gene. This second gene, comprising the cDNA for a reporter protein, such as firefly luciferase (LUC), is controlled by an appropriate hormone responsive promoter containing a hormone response element (HRE).

This reporter plasmid functions as a reporter for the transcription-modulating activity of the target IR. Thus, the reporter acts as a surrogate for the products (mRNA then protein) normally expressed by a gene under control of the target receptor and its native hormone.

The co-transfection assay can detect small molecule agonists or antagonists of target IRs. Exposing the transfected cells to an agonist ligand compound increases reporter activity in the transfected cells. This activity can be conveniently measured, e.g., by increasing luciferase production, which reflects compound-dependent, IR-mediated increases in reporter transcription. To detect antagonists, the co-transfection assay is carried out in the presence of a constant concentration of an agonist to the target IR (e.g., all-trans retinoic acid for RARα) known to induce a defined reporter signal. Increasing concentrations of a suspected antagonist will decrease the reporter signal (e.g., luciferase production). The co-transfection assay is therefore useful to detect both agonists and antagonists of specific IRs. Furthermore, it determines not only whether a compound interacts with a particular IR, but whether this interaction mimics (agonizes) or blocks (antagonizes) the effects of the native regulatory molecules on target gene expression, as well as the specificity and strength of this interaction.

The activity of the retinoid antagonist compounds of the present invention were evaluated utilizing the co-transfection assay according to the following illustrative Example 9.

EXAMPLE 9
Co-transfection Assay

CV-1 cells (African green monkey kidney fibroblasts) were cultured in the presence of Dulbecco's Modified Eagle Medium (DMEM) supplemented with 10% charcoal resin-stripped fetal bovine serum then transferred to 96-well microtiter plates one day prior to transfection.

To determine RAR and/or RXR agonist activity of the compounds of the present invention, the CV-1 cells were transiently transfected by calcium phosphate coprecipitation according to the procedure of Berger et al., 41 *J. Steroid Biochem. Mol. Biol.*, 733 (1992) with the following receptor expressing plasmids: pRShRARα: Giguere et al., 330 *Nature*, 624 (1987); pRShRARβ and pRShRARγ, Ishikawa et al., 4 *Mol. Endocrin.*, 837 (1990); pRShRXRα, Mangelsdorf et al., 345 *Nature*, 224 (1990); and pRSmRXRβ and pRSmRXRγ, Mangelsdorf et al., 6 *Genes & Devel.*, 329 (1992), the disclosures of which are herein incorporated by reference. Each of these receptor expressing plasmids was co-transfected at a concentration of 5 ng/well, along with a basal reporter plasmid at 100 ng/well, the internal control plasmid pRS-β-Gal at 50 ng/well and filler DNA, pGEM at 45 ng/well.

The basal reporter plasmid D-MTV-LUC (Hollenberg and Evans, 55 *Cell*, 899 (1988), the disclosure of which is herein incorporated by reference) containing two copies of the TRE-palindromic response element described in Umesono et al., 336 *Nature*, 262 (1988), the disclosure of which is herein incorporated by reference, was used in transfections for the RARs, and the reporter plasmid CRBPIIFKLUC, which contains an RXRE (retinoid X receptor response element, as described in Mangelsdorf et al., 66 *Cell*, 555 (1991), the disclosure of which is herein incorporated by reference), was used in transfections for the RXRs. Each of these reporter plasmids contains the cDNA for firefly luciferase (LUC) under constitutive promoter containing the appropriate RAR or RXR response element. As noted above, pRS-β-Gal, coding for constitutive expression of *E. coli* β-galactosidase (β-Gal), was included as an internal control for evaluation of transfection efficiency and compound toxicity.

Six hours after transfection, media was removed and the cells were washed with phosphate-buffered saline (PBS). Media containing compounds of the present invention in concentrations ranging from $10^{-12}$ to $10^{-5}$ M were added to the cells. Similarly, the reference compounds [all-trans retinoic acid (ATRA)(Sigma Chemical), a known RAR selective compound, and 9-cis retinoic acid (9-cis)(synthesized as described in Heyman et al., *Cell*, 68:397–406 (1992)), a compound with known activity on RARs and RXRs, were added at similar concentrations to provide a reference point for analysis of the activity of the compounds of the present invention. Retinoid purity was established as greater than 99% by reverse phase high-performance liquid chromatography. Retinoids were dissolved in dimethylsulfoxide for use in the transcriptional activation assays. Three to four replicates were used for each sample. When determining the antagonist activity of the compounds of the present invention, the compounds were added to the cells in the presence of a fixed concentration ($3.2 \times 10^{-8}$ M) of the known RXR agonist TARGRETIN™ (LGD1069)(4-[(3,5,5,8,8-Pentamethyl-5,6,7,8-tetrahydro-2-naphthyl)ethenyl]benzoic acid: Ligand Pharmaceuticals, Inc.) or the known RAR agonist compound TTNPB. Retinoid purity was established as greater than 99% by reverse phase high-performance liquid chromatography. Retinoids were dissolved in dimethylsulfoxide for use in the transcriptional activation assays. Three to four replicates were used for each sample. Transfections and subsequent procedures were performed on a Biomek 1000 automated work station.

After 40 hours, the cells were washed with PBS, lysed with a Triton X-100-based buffer and assayed for LUC and β-Gal activities using a luminometer or spectrophotometer, respectively. For each replicate, the normalized response (NR) was calculated as:

$$\text{LUC response}/\beta\text{-Gal rate}$$

where β-Gal rate=β-Gal•$1 \times 10^{-5}$/β-Gal incubation time.

The mean and standard error of the mean (SEM) of the NR were calculated. Data was plotted as the response of the compound compared to the reference compounds over the range of the dose-response curve. For the agonist compounds of the present invention, the effective concentration that produced 50% of the maximum response ($EC_{50}$) was quantified. Antagonist activity was determined by testing the amount of LUC expression in the presence of the RAR and/or RXR agonists described above at the $EC_{50}$ concentration for such known compounds. The concentration of compounds of the present invention that inhibited 50% of LUC expression induced by the reference agonist was quantified ($IC_{50}$). In addition, the efficacy of antagonists was determined as a function (%) of maximal inhibition.

RXR and RAR Binding

In addition to the cotransfection data, the binding of selected compounds of the present invention to the RAR and RXR receptors was also investigated according to the methodology described in M. F., Boehm, et al., "Synthesis and Structure-Activity Relationships of Novel Retinoid X Receptor Selective Retinoids", 37 *J. Med. Chem.*, 2930 (1994); M. F. Boehm, et al., "Synthesis of High Specific Activity [$^3$H]-9-cis Retinoic Acid and Its Application for Identifying Retinoids with Unusual Binding Properties", 37 *J. Med. Chem.*, 408 (1994), and E. A. Allegretto, et al., "Characterization and Comparison of Hormone-Binding and Transactivation Properties of Retinoic Acid and Retinoid X Receptors Expressed in Mammalian Cells and Yeast", 268 *J. Biol. Chem.*, 22625 (1993), the disclosures of which are herein incorporated by reference.

Non-specific binding was defined as that binding remaining in the presence of 500 nM of the appropriate unlabelled compound. At the end of the incubation period, bound from free ligand were separated. The amount of bound tritiated retinoids was determined by liquid scintillation counting of an aliquot (700 μL) of the supernatant fluid or the hydroxylapatite pellet.

After correcting for non-specific binding, $IC_{50}$ values were determined. The $IC_{50}$ value is defined as the concentration of competing ligand needed to reduce specific binding by 50%. The $IC_{50}$ value was determined graphically from a log-logit plot of the data. The $K_d$ values were determined by application of the Cheng-Prussof equation to the $IC_{50}$ values, the labeled ligand concentration and the $K_d$ of the labeled ligand.

The $IC_{50}$ antagonist potency (nM), $EC_{50}$ agonist potency (nM) and binding activity (Kd in nM) of selected RAR retinoid antagonist compounds of the present invention on RARα,β,γ and RXRα,β,γ are shown in Table 1 below. The activity of the antagonist compounds are compared to the known RAR agonist TTNPB, and to compound A, covered by PCT Application No. WO 96/20913, that is somewhat structurally related, but displays only activity as an RAR? agonist.

TABLE 1

Potency (nM) and binding ($K_d$) of selected RAR antagonist compounds of the present invention on RARα,β,γ and RXRα,β,γ in comparison to the known RAR-active retinoid compound TTNPB and compound A.

| Cmpd. No. | Activity (nM) | RARα | RARβ | RARγ | RXRα,β,γ |
|---|---|---|---|---|---|
| A (OCH$_3$ at R$^2$) | $IC_{50}$ nM | na | na | — | na |
|  | $EC_{50\ nM}$ | na | 1 | 1 | na |
|  | $K_d$ | 1 | 0.4 | 0.5 | na |
| 7 | $IC_{50}$ nM | 4 (90) | 4 (85) | 2 (91) | na |
|  | $EC_{50\ nM}$ | na | na | na | na |
|  | $K_d$ | 3 | 5 | 17 | na |
| 8 | $IC_{50}$ nM | 2 (90) | 1 (85) | 3 (85) | na |
|  | $EC_{50\ nM}$ | na | na | na | na |
|  | $K_d$ | 2 | 1 | 4 | na |
| 9 | $IC_{50}$ nM | 5 (91) | 17 (86) | 5 (80) | na |
|  | $EC_{50\ nM}$ | na | na | na | na |
|  | $K_d$ | 9 | 5 | 14 | na |
| 17 | $IC_{50}$ nM | 2 (98) | 5 (90) | 2 (85) | na |
|  | $EC_{50\ nM}$ | na | na | na | na |
|  | $K_d$ | 2 | 3 | 14 | na |
| TTNPB | $IC_{50}$ nM | na | na | na | na |
|  | $EC_{50\ nM}$ | 45 | 5 | 2 | na |
|  | $K_d$ | 20 | 39 | 51 | na | na = not active if potency of >10,000 and/or efficacy of <20% and/or binding of >1,000

EXAMPLE 10

The following examples provide illustrative pharmacological composition formulations:

Hard gelatin capsules are prepared using the following ingredients:

|  | Quantity (mg/capsule) |
|---|---|
| Compound 8 | 140 |
| Starch, dried | 100 |
| Magnesium stearate | 10 |
| Total | 250 mg |

The above ingredients are mixed and filled into hard gelatin capsules in 250 mg quantities.

A tablet is prepared using the ingredients below:

|  | Quantity (mg/tablet) |
|---|---|
| Compound 8 | 140 |
| Cellulose, microcrystalline | 200 |
| Silicon dioxide, fumed | 10 |
| Stearic acid | 10 |
| Total | 360 mg |

The components are blended and compressed to form tablets each weighing 360 mg.

Tablets, each containing 60 mg of active ingredient, are made as follows:

|  | Quantity (mg/tablet) |
|---|---|
| Compound 8 | 60 |
| Starch | 45 |
| Cellulose, microcrystalline | 35 |
| Polyvinylpyrrolidone (PVP) (as 10% solution in water) | 4 |
| Sodium carboxymethyl starch (SCMS) | 4.5 |
| Magnesium stearate | 0.5 |
| Talc | 1.0 |
| Total | 150 mg |

The active ingredient, starch, and cellulose are passed through a No. 45 mesh U.S. sieve and mixed thoroughly. The solution of PVP is mixed with the resultant powders, which are then passed through a No. 14 mesh U.S. sieve. The granules so produced are dried at 50° C. and passed through a No. 18 mesh U.S. sieve. The SCMS, magnesium stearate, and talc, previously passed through a No. 60 mesh U.S. sieve, are then added to the granules which, after mixing, are compressed on a tablet machine to yield tablets each weighing 150 mg.

Suppositories, each containing 225 mg of active ingredient, may be made as follows:

| Compound 8 | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of normal 2 g capacity and allowed to cool.

An intravenous formulation may be prepared as follows:

| Compound 8 | 100 mg |
|---|---|
| Isotonic saline | 1,000 ml |
| Glycerol | 100 ml |

The compound is dissolved in the glycerol and then the solution is slowly diluted with isotonic saline. The solution of the above ingredients is then administered intravenously at a rate of 1 ml per minute to a patient.

While in accordance with the patent statutes, description of the preferred embodiments and processing conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following claims.

What is claimed is:

1. A compound of the formula:

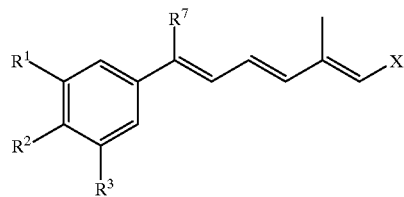

wherein:
R$^1$ and R$^3$ each independently are a C$_3$–C$_{10}$ alkyl, fluoroalkyl or perfluoroalkyl, an optionally substituted aryl, heteroaryl or arylalkyl, NR$^4$ or NR$^4$R$^5$, where R$^4$ and R$^5$ each independently are a C$_1$–C$_6$, alkyl, fluoroalkyl or perfluoroalkyl, or when R$^1$ is any of the above, then R$^3$ can be OR$^6$, where R$^6$ is a C$_3$–C$_{12}$ alkyl, fluoroalkyl or perfluoroalkyl;
R$^2$ is an optionally substituted aryl, heteroaryl, a C$_4$–C$_{12}$ alkyl, fluoroalkyl or perfluoroalkyl optionally substituted with $^{14}$CH$_3$, $^{13}$CH$_3$, CD$_3$, C$^3$H$_3$, and/or $^{13}$CD$_3$, OR$^6$, where R$^6$ has the definition given above, or R$^2$ can be hydrogen, OCH$_3$ or OCH$_2$CH$_3$ if R$^1$ and/or R$^3$ are an aryl or heteroaryl linked by a C$_1$–C$_{12}$ alkyl, fluoroalkyl or perfluoroalkyl;
R$^7$ is hydrogen, F, Cl, Br, I, CF3 or a C$_1$–C$_2$ alkyl optionally substituted with $^{14}$CH$_3$, $^{13}$CH$_3$, CD$_3$, C$^3$H$_3$, and/or $^{13}$CD$_3$;
X is COOR$^8$, CONR$^9$, or CONHR$^9$R$^{10}$ where R$^8$ represents hydrogen or a C$_1$–C$_6$ alkyl, and where R$^9$ and R$^{10}$ each independently represent a C$_1$–C$_6$ alkyl, or an aryl or heteroaryl optionally substituted with OH, F, Br, Cl or I, provided, however, that R$^9$ and R$^{10}$ both cannot be an aryl or heteroaryl.

2. A compound according to claim 1, selected from the group consisting of, 2E, 4E, 6E-[7-(3,5-Di-t-butyl-4-n-butoxyphenyl)-3-methyl]-octa-2,4,6-trienoic acid; 2E, 4E, 6E-[7-(3,5-Di-t-butyl-4-n-propoxyphenyl)-3-methyl]-octa-2,4,6-trienoic acid; 2E, 4E, 6E-[7-(3,5-Di-t-butyl-4-n-pentoxyphenyl)-3-methyl]-octa-2,4,6-trienoic acid; 2E, 4E, 6E-[7-(3,5-Di-t-butyl-4-n-hexoxyphenyl)-3-methyl]-octa-2,4,6-trienoic acid; 2E, 4E, 6E-[7-(3,5-Di-t-butyl-4-n-heptoxyphenyl)-3-methyl]-octa-2,4,6-trienoic acid; 2E, 4E, 6E-[7-(3,5-Di-t-butyl-4-n-octoxyphenyl)-3-methyl]-octa-2,4,6-trienoic acid; (2E,4E,6E)-7-[3-t-butyl-5-(1-phenyl-vinyl)-phenyl]-3-methyl-octa-2,4,6-trienoic acid; and 2E, 4E, 6E-[7-(3,5-Di-t-butyl-4-{[4,5-$^3$H$_2$]-n-pentoxy}phenyl)-3-methyl]-octa-2,4,6-trienoic acid.

3. A compound according to claim 1, wherein R$^1$ and R$^3$ independently represent a C$_3$–C$_{10}$ alkyl and R$^2$ represents a C$_4$–C$_8$ alkyl.

4. A compound according to claim 3, wherein R$^1$ and R$^3$ independently represent a C$_3$–C$_4$ alkyl and R$^2$ represents a C$_4$–C$_6$ alkyl.

5. A compound according to claim 1, wherein the compound is a RAR antagonist.

6. A compound according to claim 5, wherein the compound exhibits 50% maximal inhibition of one or more RARs at a concentration of less than 100 nM.

7. A compound according to claim 5, wherein the compound exhibits 50% maximal inhibition of one or more RARs at a concentration of less than 50 nM.

8. A compound according to claim 5, wherein the compound exhibits 50% maximal inhibition of one or more RARs at a concentration of less than 20 nM.

9. A compound according to claim 5, wherein the compound exhibits 50% maximal inhibition of one or more RARs at a concentration of less than 10 nM.

10. A compound according to claim 5, wherein the compound is a selective RAR antagonist.

11. A compound according to claim 1, wherein the compound is administered to a patient as a dosage unit at from about 1 μg/kg of body weight to about 500 mg/kg of body weight.

12. A compound according to claim 1, wherein the compound is administered to a patient as a dosage unit at from about 10 μg/kg of body weight to about 250 mg/kg of body weight.

13. A compound according to claim 1, wherein the compound is administered to a patient as a dosage unit at from about 20 μg/kg of body weight to about 100 mg/kg of body weight.

14. A compound according to claim 5, wherein the compound is effective in treating hypervitaminosis A syndrome, and RAR agonist side effects selected from the group consisting of headache, skin irritation, skin peeling, bone toxicities, dislipidemias, teratogenesis, mucocutaneous toxicity, musculoskeletal toxicity, and hepatotoxicity.

15. A pharmaceutical composition comprising a compound of claim 1 and a pharmaceutically acceptable carrier.

16. A pharmaceutical composition according to claim 15, wherein the composition is formulated for oral, topical, intravenous, suppository or parental administration.

17. A pharmaceutical composition according to claim 15, wherein the compound is administered to a patient as a dosage unit at from about 1 μg/kg of body weight to about 500 mg/kg of body weight.

18. A pharmaceutical composition according to claim 15, wherein the compound is administered to a patient as a dosage unit at from about 10 μg/kg of body weight to about 250 mg/kg of body weight.

19. A pharmaceutical composition according to claim 15, wherein the compound is administered to a patient as a dosage unit at from about 20 μg/kg of body weight to about 100 mg/kg of body weight.

20. A pharmaceutical composition according to claim 15, wherein the composition is effective in treating hypervitaminosis A syndrome, and RAR agonist side effects selected from the group consisting of headache, skin irritation, skin peeling, bone toxicities, dislipidemias, teratogenesis, mucocutaneous toxicity, musculoskeletal toxicity, and hepatotoxicity.

21. A method of modulating processes mediated by RAR receptors comprising administering to a patient an amount of a compound according to claim 1, said amount being effective to modulate one or more processes mediated by RARs.

22. A method of modulating according to claim 21, wherein the compound is effective to antagonize one or more processes mediated by RARs.

23. A method of treating a patient requiring RAR antagonist therapy comprising administering to the patient a pharmaceutically effective amount of a compound according to claim 1.

24. A method of treating a patient according to claim 23, further comprising prior, subsequent or co-administration of an RAR agonist compound.

25. A method of treating a patient according to claim 23, wherein the compound is effective in treating hypervitaminosis A syndrome, and RAR agonist side effects selected from the group consisting of headache, skin irritation, skin peeling, bone toxicities, dislipidemias, teratogenesis, mucocutaneous toxicity, musculoskeletal toxicity, and hepatotoxicity.

26. A method of treating a patient requiring RAR antagonist therapy comprising administering to the patient a pharmaceutically effective amount of a composition according to claim 15.

27. A method of treating a patient according to claim 26, further comprising prior, subsequent or co-administration of an RAR agonist compound.

28. A method of treating a patient according to claim 26, wherein the composition is effective in treating hypervitaminosis A syndrome, and RAR agonist side effects selected from the group consisting of headache, skin irritation, skin peeling, bone toxicities, dislipidemias, teratogenesis, mucocutaneous toxicity, musculoskeletal toxicity, and hepatotoxicity.

29. A method for determining the presence of one or more RAR receptors in a sample comprising combining a compound according to claim 1 with the sample containing one or more unknown retinoid receptors, and determining whether said compound binds to a receptor in the sample.

* * * * *